(12) United States Patent
Olson

(10) Patent No.: US 10,898,371 B2
(45) Date of Patent: Jan. 26, 2021

(54) ADJUSTABLE LOOP FIBER OPTIC ILLUMINATION DEVICE FOR SURGERY

(71) Applicant: The Regents of the University of Colorado, a body corporate, Denver, CO (US)

(72) Inventor: Jeffrey L. Olson, Cherry Hills Village, CO (US)

(73) Assignee: The Regents of the University of Colorado, Denver, CO (US)

(*) Notice: Subject to any disclaimer, the term of this patent is extended or adjusted under 35 U.S.C. 154(b) by 76 days.

(21) Appl. No.: 16/209,470

(22) Filed: Dec. 4, 2018

(65) Prior Publication Data

US 2019/0175398 A1    Jun. 13, 2019

Related U.S. Application Data

(63) Continuation of application No. 14/438,532, filed as application No. PCT/US2013/066837 on Oct. 25, 2013, now Pat. No. 10,179,067.

(60) Provisional application No. 61/718,543, filed on Oct. 25, 2012.

(51) Int. Cl.
| | |
|---|---|
| *A61F 9/007* | (2006.01) |
| *A61B 3/00* | (2006.01) |
| *A61B 90/30* | (2016.01) |

(52) U.S. Cl.
CPC ............ *A61F 9/007* (2013.01); *A61B 3/0008* (2013.01); *A61B 90/30* (2016.02); *A61B 2090/306* (2016.02)

(58) Field of Classification Search
CPC ... A61F 9/0007; A61B 3/0008; A61B 3/0075; A61B 90/30; A61B 2090/306

USPC .............................................. 385/13; 600/249
See application file for complete search history.

(56) References Cited

U.S. PATENT DOCUMENTS

| | | | | |
|---|---|---|---|---|
| 4,326,530 A | * | 4/1982 | Fleury, Jr. ........ | A61B 17/32056 606/47 |
| 5,123,906 A | | 6/1992 | Kelman | |
| 5,163,942 A | * | 11/1992 | Rydell ............ | A61B 17/32056 606/1 |
| 5,171,314 A | * | 12/1992 | Dulebohn ........ | A61B 17/32056 606/110 |
| 5,417,684 A | * | 5/1995 | Jackson ........... | A61B 17/00234 606/1 |
| 5,822,036 A | * | 10/1998 | Massie ................... | A61B 3/125 351/219 |
| 6,221,028 B1 | * | 4/2001 | Lieberman ........... | A61B 3/0008 351/200 |

(Continued)

FOREIGN PATENT DOCUMENTS

| | | |
|---|---|---|
| JP | H0451946 | 2/1992 |
| WO | WO2008/124492 A1 | 10/2008 |

(Continued)

OTHER PUBLICATIONS

Extended European Search Report and Search Opinion dated May 10, 2016 for European Application No. 13849319.2.

*Primary Examiner* — Eric S Gibson
(74) *Attorney, Agent, or Firm* — Perkins Coie LLP

(57) ABSTRACT

The present disclosure provides an adjustable endoscopic surgical device for illuminating a tissue surface with diffuse and oblique light. In some embodiments, light emanates from the sides of an optical fiber, which is optionally formed at least in part into a loop shape.

17 Claims, 5 Drawing Sheets

(56) References Cited

U.S. PATENT DOCUMENTS

| | | | | |
|---|---|---|---|---|
| 6,367,984 | B1* | 4/2002 | Stephenson | G02B 6/3825 385/53 |
| 6,676,668 | B2* | 1/2004 | Mercereau | A61B 17/221 606/1 |
| 7,197,931 | B2* | 4/2007 | Kim | G01H 9/004 250/227.18 |
| 7,428,350 | B1* | 9/2008 | Varadarajan | E21B 47/135 385/13 |
| 7,985,028 | B2* | 7/2011 | Aoki | G02B 6/2551 385/39 |
| 8,771,297 | B2* | 7/2014 | Miller | A61B 17/0467 606/148 |
| 8,974,473 | B2* | 3/2015 | Kaplan | A61B 17/10 606/139 |
| 9,265,526 | B1* | 2/2016 | Abdou | A61B 17/3439 |
| 9,433,475 | B2* | 9/2016 | Bierbaum | A61C 1/0046 |
| 9,498,206 | B2* | 11/2016 | Fung | A61B 17/12013 |
| 9,936,956 | B2* | 4/2018 | Fung | A61B 17/12013 |
| 10,179,067 | B2* | 1/2019 | Olson | A61B 90/30 |
| 2006/0184162 | A1* | 8/2006 | Smith | A61B 90/36 606/4 |
| 2007/0100326 | A1* | 5/2007 | Smith | A61F 9/007 606/4 |
| 2007/0293748 | A1* | 12/2007 | Engvall | A61B 5/0059 600/371 |
| 2010/0228119 | A1* | 9/2010 | Brennan | A61B 3/10 600/424 |
| 2011/0044577 | A1* | 2/2011 | Gupta | G01M 5/0033 385/13 |
| 2011/0144641 | A1* | 6/2011 | Dimalanta, Jr. | A61F 9/00736 606/45 |
| 2011/0144745 | A1* | 6/2011 | Martin | A61B 3/0008 623/4.1 |
| 2012/0022424 | A1* | 1/2012 | Yamamoto | A61F 9/00781 604/8 |
| 2012/0165941 | A1* | 6/2012 | Rabiner | A61B 17/8802 623/17.12 |
| 2014/0288417 | A1* | 9/2014 | Schmidtlin | A61B 5/0066 600/425 |
| 2015/0025325 | A1* | 1/2015 | Lee | A61B 1/07 600/249 |
| 2015/0282888 | A1* | 10/2015 | Olson | A61B 90/30 600/249 |
| 2015/0351958 | A1* | 12/2015 | Contiliano | A61F 9/0017 604/521 |
| 2017/0014023 | A1* | 1/2017 | Kern | A61M 5/14 |
| 2019/0175398 | A1* | 6/2019 | Olson | A61F 9/007 |

FOREIGN PATENT DOCUMENTS

| | | |
|---|---|---|
| WO | WO2011/081525 A1 | 7/2011 |
| WO | WO2011/150045 A1 | 12/2011 |

* cited by examiner

ADJUSTABLE LOOP FIBER OPTIC
ILLUMINATION DEVICE FOR SURGERY

PRIORITY CLAIM

This application is a continuation of U.S. patent application Ser. No. 14/438,532 filed Apr. 24, 2015, which is a U.S. 371 national stage of International Patent Application No. PCT/US2013/066837 filed Oct. 25, 2013, which claims priority to U.S. patent application Ser. No. 61/718,543 filed Oct. 25, 2012 the entire contents of each of which are incorporated herein by reference and relied upon.

BACKGROUND

During intraocular or endoscopic surgery, a surgeon may need to alter both the intensity and the direction of light in order to better visualize the surgical field. Conventional light sources often work similar to a flashlight, with a directed beam that focuses light directly on a specific area. This direct illumination prevents the surgeon from fully visualizing any texture or surface irregularities. Consequently, surgeons often employ special stains or dyes to help visualize the surgical field. For example, during vitreoretinal surgery for an epiretinal membrane, direct illumination of the membrane is often inadequate to visualize the tissue, so vital stains may be used to increase visibility of the tissue.

Handheld lights that provide direct illumination typically have a field of illumination of about 50 to 80 degrees. This direct illumination fails to highlight the texture of a surface. Further, reducing the distance between the light and the surface of the retina increases the risk of phototoxicity to retinal photoreceptors. Wide-field chandelier lighting systems typically have a 100 degree field of illumination, but are placed at a fixed distance from the retina and therefore cannot provide side illumination to highlight surface texture. Further, chandeliers cast shadows when working instruments are placed in front of them and are also prone to creating glare during air-fluid exchanges such as those required during vitrectomy. Further, chandeliers are often incapable of homogenously illuminating the entire eye, and often need to be repositioned during surgery. Further, the tips of chandelier lights or probes are prone to melting if they come into contact with blood or uveal tissue. Existing fiber optic illumination systems provide direct or wide-field illumination only. A need exists for improved surgical lighting system, especially those effective for visualizing the surface details of ocular tissue.

SUMMARY

This adjustable fiber optic illumination device invention allows the surgeon to adjust both the direction and the intensity of light intraoperatively, so that the surgical field can be illuminated from the side or in a more diffuse manner, thereby increasing contrast and visualization of surface texture and irregularities, thereby eliminating or reducing the need for intraoperative stains or dyes.

Accordingly, the present disclosure provides a surgical illumination device comprising an optical fiber extending through the lumen and comprising a distal end and a proximal end; a stem comprising a lumen, wherein the optical fiber and the proximal end are housed within the lumen to form a loop portion defining a loop length; an adjuster operably coupled to the proximal end, wherein movement of the adjuster causes the loop length to change; and a light source operably coupled to the distal end.

In some embodiments, the present disclosure provides a method of illuminating ocular tissue, the method comprising providing a device as described herein; optionally increasing the loop length such that the loop portion has a diameter larger than an eye or a portion thereof; placing the loop portion in proximity to the eye; and reducing the loop length such that the loop portion is stationary with respect to the eye.

DETAILED DESCRIPTION

Figure 1:
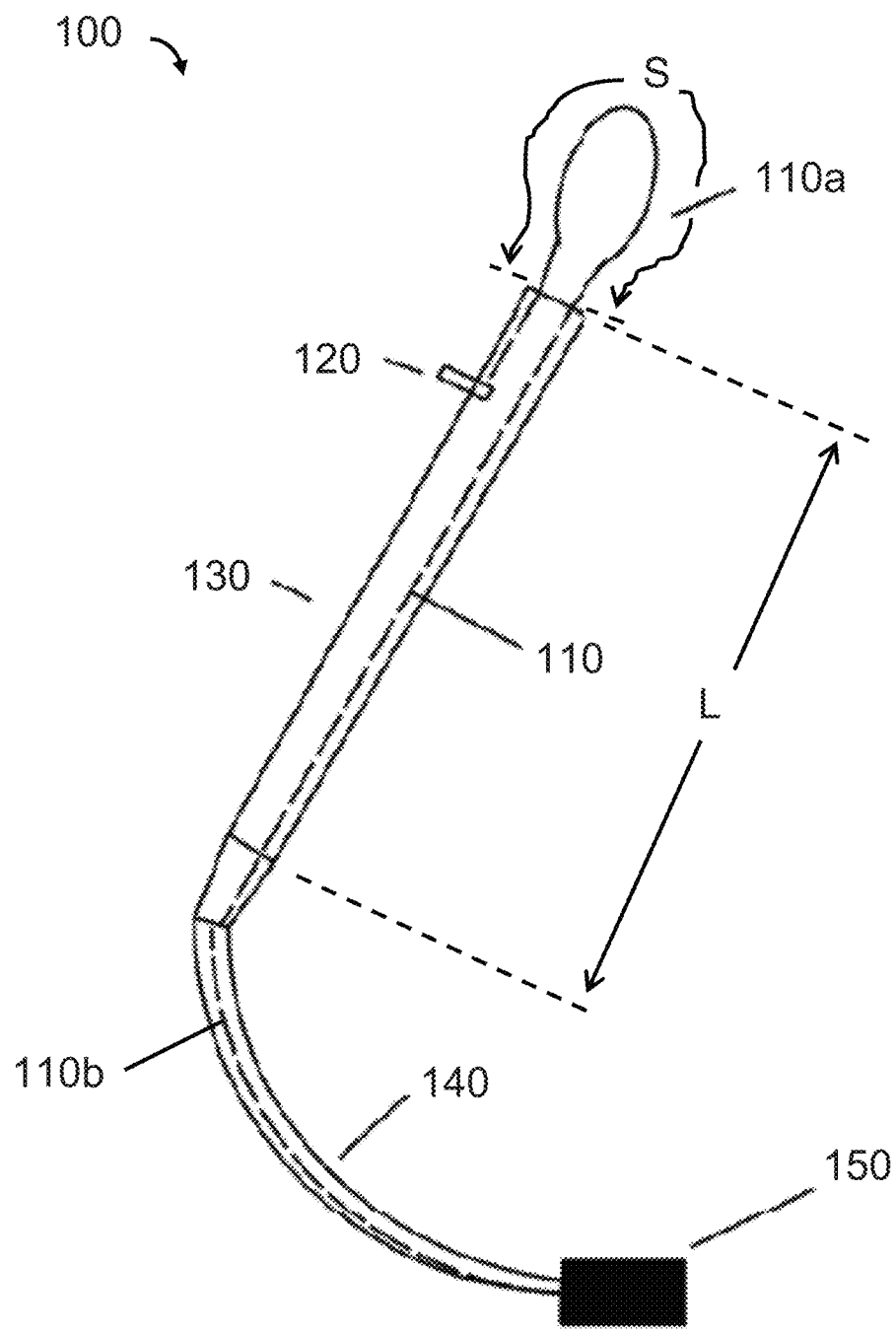
FIG. 1 illustrates one embodiment of a device according to the present disclosure.

In some embodiments, the present disclosure provides a device comprising a stem operably linked to a light source by a fiber optic cable. An optical fiber (also referred to as a fiber optic or a fiber optic element) passes through a lumen of the stem and a tip of the fiber optic is passed back into the lumen of the stem such that a loop is formed in the fiber optic. The tip of the fiber optic is operably coupled to an adjuster (e.g., a lever) which, when adjusted, causes the length of the fiber optic forming the loop portion to increase or decrease as needed. A second tip of the fiber optic is operably coupled to a light source, such as that associated with an endoscope. In some embodiments, the fiber optic and the endoscope are operably coupled by an adapter.

In some embodiments, the stem has a length of about 4 to 6 inches in length, for example about 4 inches, about 4.1 inches, about 4.2 inches, about 4.3 inches, about 4.4 inches, about 4.5 inches, about 4.6 inches, about 4.7 inches, about 4.8 inches, about 4.9 inches, about 5 inches, about 5.1 inches, about 5.2 inches, about 5.3 inches, about 5.4 inches, about 5.5 inches, about 5.6 inches, about 5.7 inches, about 5.8 inches, about 5.9 inches, or about 6 inches.

In some embodiments, the stem is a hollow tube shape having a regular or irregular cross-section, such as a circle, an oval, an ellipse, a square, a rounded square, etc. Generally, the stem has a cross-sectional area sufficient to permit the fiber optic to pass through (or partially pass through) at least two times. For vitrectomy surgery, the diameter of the stem may range from about 18 gauge to about 30 gauge, for example about 18 gauge, about 19 gauge, about 20 gauge, about 21 gauge, about 22 gauge, about 23 gauge, about 24 gauge, about 25 gauge, about 26 gauge, about 27 gauge, about 28 gauge, about 29 gauge, or about 30 gauge.

In some embodiments, the optical fiber is a flexible rod. In some embodiments, the optical fiber comprises, consists of, or consists essentially of glass, silica, or plastic. In some embodiments, the optical fiber has a diameter of about 50 µm to about 1000 µm, for example about 50 µm, about 60 µm, about 70 µm, about 80 µm, about 90 µm, about 100 µm, about 110 µm, about 120 µm, about 130 µm, about 140 µm, about 150 µm, about 160 µm, about 170 µm, about 180 µm, about 190 µm, about 200 µm, about 210 µm, about 220 µm, about 230 µm, about 240 µm, about 250 µm, about 260 µm, about 270 µm, about 280 µm, about 290 µm, about 300 µm, about 310 µm, about 320 µm, about 330 µm, about 340 µm, about 350 µm, about 360 µm, about 370 µm, about 380 µm, about 390 µm, about 400 µm, about 410 µm, about 420 µm, about 430 µm, about 440 µm, about 450 µm, about 460 µm, about 470 µm, about 480 µm, about 490 µm, about 500 µm, about 510 µm, about 520 µm, about 530 µm, about 540 µm, about 550 µm, about 560 µm, about 570 µm, about 580 µm, about 590 µm, about 600 µm, about 610 µm, about 620 µm, about 630 µm, about 640 µm, about 650 µm, about 660 µm, about 670 µm, about 680 µm, about 690 µm, about 700 µm, about 710 µm, about 720 µm, about 730 µm, about 740 µm, about 750 µm, about 760 µm, about 770 µm, about 780 µm, about 790 µm, about 800 µm, about 810 µm, about 820 µm, about 830 µm, about 840 µm, about 850 µm, about 860 µm, about 870 µm, about 880 µm, about 890 µm, about 900 µm, about 910 µm, about 920 µm, about 930 µm, about 940 µm, about 950 µm, about 960 µm, about 970 µm, about 980 µm, about 990 µm, or about 1000 µm.

In some embodiments, light emanates from the sides or wall of the device depending upon its construction. In some embodiments, the optical fiber is housed in a cable, which contains the optical fiber and connects the stem of the device to a suitable light source via an adapter. The optical fiber extends through the lumen of the stem. The end of the optical fiber is attached to a lever, and a loop of the optical fiber passes out the distal end of the stem. It is this exposed portion of the optical fiber which illuminates the surgical field. The loop is retractable and expandable, thereby changing the amount of illumination, by sliding the lever and causing the size of the loop outside the stem to increase or decrease in diameter.

The optical fiber is necessary to transmit light from a suitable light source to the surgical field. The stem and cable are both necessary to house the optical fiber. The lever is necessary to change the size of the fiber optic loop outside the stem. In one embodiment, the lever could be removed, leaving a fixed amount of loop exposed.

In some embodiments, the tip of the optical fiber is operably coupled to a button or a sliding shaft instead of a lever. Alternatively, a sliding cover could be placed over the stem itself, whereby adjustment of the loop portion is achieved by advancing or retracting the sliding cover relative to the stem.

In some embodiments, the stem further comprises a flange suitable for anchoring the device in place when attached to or passed through the sclera.

In another embodiment, two or more optical fiber elements emanate from the of the stem, thus forming two or more fiber optic loop portions.

Thus, in one embodiment, the present disclosure provides surgical device comprising an optical fiber, wherein the optical fiber comprises a loop. In some embodiments, at least a portion of the optical fiber is housed in a stem. In some embodiments, a proximal end of the optical fiber is operably coupled to an adjuster. In some embodiments, the adjuster is configured to adjust a size associated with the loop. In some embodiments, the adjuster comprises a lever, a button, a sliding shaft or a sliding cover.

In another embodiment, the present disclosure comprises a surgical illumination device comprising an optical fiber extending through the lumen and comprising a distal end and a proximal end; a stem comprising a lumen, wherein the optical fiber and the proximal end are housed within the lumen to form a loop portion defining a loop length; and an adjuster operably coupled to the proximal end, wherein movement of the adjuster causes the loop length to change, wherein the distal end of the optical fiber is configured for coupling to a light source. In some embodiments, the surgical illumination device comprises an optical fiber cable surrounding at least a portion of the optical fiber. In some embodiments, the adjuster is a lever, a button, a sliding shaft or a sliding cover. In some embodiments, the stem comprises a flange configured to and suitable for anchoring the device in or through ocular tissue.

In some embodiments, a device as disclosed herein comprises or is configured in a first mode wherein light emanates from the loop and comprises or is configured in a second configuration wherein light emanates from a tip of the optical fiber. In some embodiments, the device is configured to convert from the first configuration to the second configuration during surgery.

FIG. 1 illustrates a device 100 according to the present disclosure including an optical fiber 110 comprising a fiber optic loop portion 110*a*. The optical fiber 110 has a proximal end 112 that is operably connected to an adjuster 120. The adjuster 120 is housed in a stem 130 which is configured to allow the adjuster 120 to slide along the length L of stem 130. Movement of the adjuster 120 along length L of the stem 130 causes the size S of the fiber optic loop 110*a* to change. A distal end of stem 130 is operably connected to a fiber optic cable 140 that houses a distal end portion 110*b* of the optical fiber 110. An adapter 150 is connected to the fiber optic cable 140 and enables the device 110 to be connected to a light source (not shown).

Figure 2:
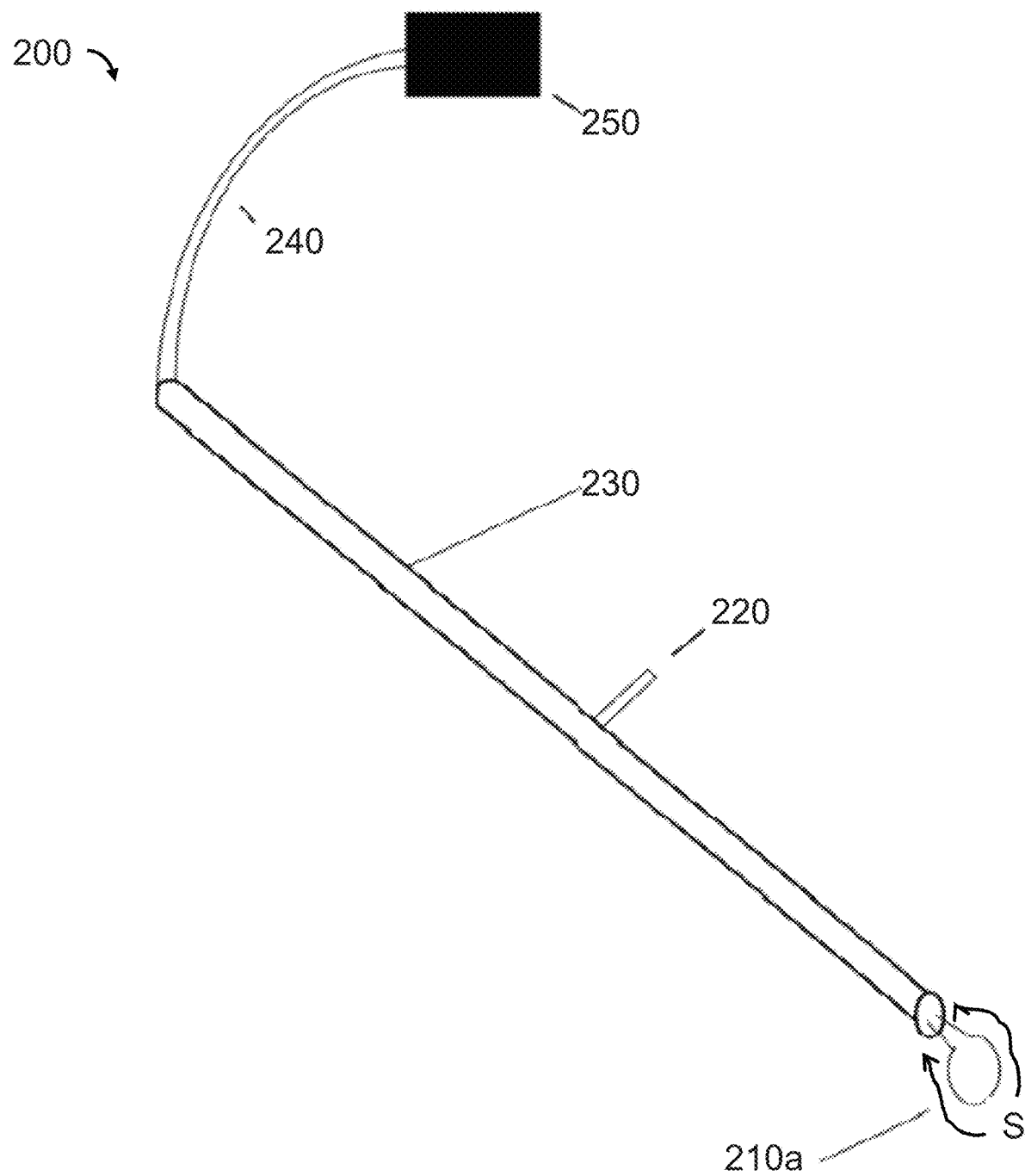
FIG. 2 illustrates another embodiment of a device according to the present disclosure.

FIG. 2 shows an external view of another embodiment of the present disclosure. In this embodiment, device 200 includes a fiber optic loop portion 210*a* extends from a stem 230 that is configured with an adjuster 220 that is a lever. Movement of the adjuster 220 changes the size S of the fiber optic loop portion 210*a*. Stem 230 is operably connected to a fiber optic cable 240 which in turn is connected to an adapter 250 that enables device 200 to be connected to a light source.

Figure 3C:
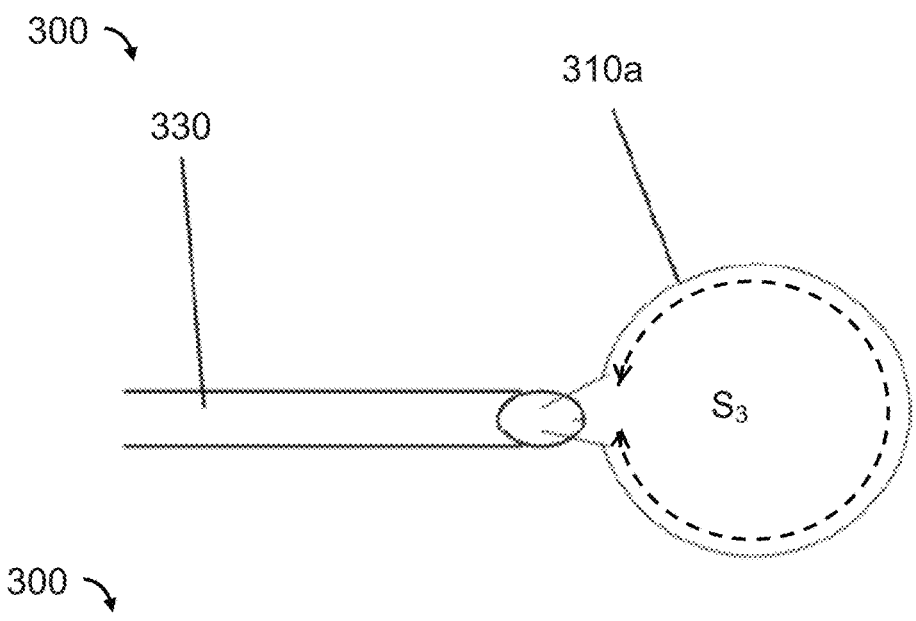
FIGS. 3A-3C depict an embodiment of a device according to the present invention wherein the size of the fiber optic loop is adjustable from a small size (FIG. 3A) to an intermediate size (FIG. 3B) to a large size (FIG. 3C), or vice versa.
Figure 3B:
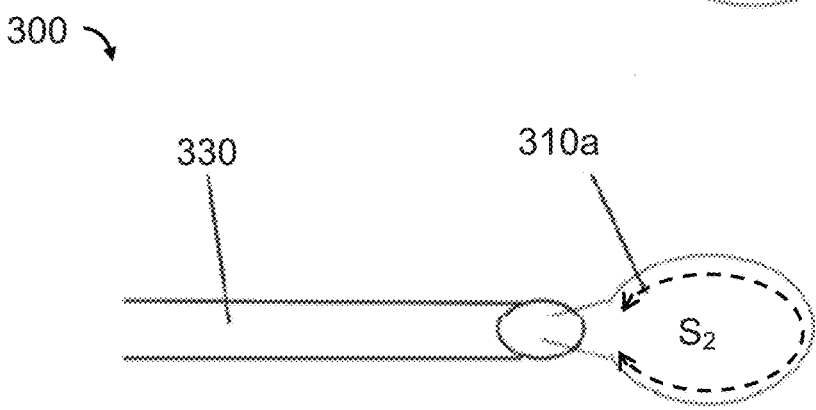
Figure 3A:
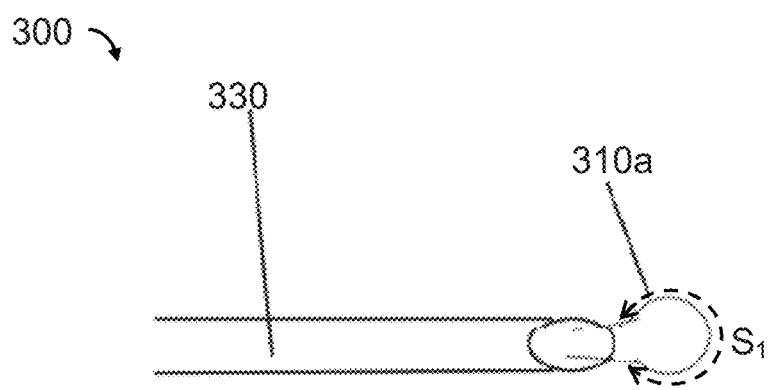

FIGS. 3*a*-3*c* illustrate the adjustment of fiber optic loop portion 310*a* in a device 300 consistent with the present disclosure. In this embodiment, device 300 includes a stem 330 that houses an optical fiber (not shown) which includes a fiber optic loop portion 310*a*. The fiber optic loop portion 310*a* extends from a proximal end of the stem 330. Movement of an adjuster (not shown) changes the size ($S_1$-$S_3$) of the fiber optic loop portion 310*a*. For example, fiber optic loop portion 310*a* may have an initial size $S_1$ as shown in FIG. 3*a*. In some embodiments, such a configuration is useful for initial penetration or deployment of the device 300 during a surgical procedure. Movement of the adjuster (e.g., after initial deployment of the device 300 during a surgical procedure) may then cause the size of the fiber optic loop 310*a* to expand to a second size $S_2$ as shown in FIG. 3*b*. If desired, additional movement of the adjuster causes the fiber optic loop portion 310*a* to further expand to a third size $S_3$ as shown in FIG. 3*c*. Movement of the adjuster in an opposite direction may cause the fiber optic loop portion 310*a* to shrink, for example from an expanded size $S_3$ (FIG. 3*c*) to an intermediate size $S_2$ (FIG. 3*b*) and/or to a small size Si (FIG. 3*a*).

In some embodiments, the fiber optic loop could be made much larger so that it could encompass the external diameter of the eye. This loop could then be placed around the equator of the eye during vitreoretinal surgery and tightened to a sufficient length to indent the eye wall, which aids the surgeon in visualizing the periphery of the retina as is done in scleral depression. Further, the added light from this would assist in visualizing any peripheral retinal pathology.

In some embodiments, the fiber optic loop can be used as a tool for pushing, pulling, or grasping an object (e.g., a tissue or a foreign body) during a surgical procedure. In some embodiments, the device is used to repair retinal detachments during a vitrectomy. In one such embodiment, the device is passed through a small gauge trocar or surgical wound. Once inside the eye, the adjuster is used to deploy (e.g., expand) the fiber optic loop. The fiber optic loop is then used to manually push the retina back against the eye wall. During this, the subretinal fluid can be drained through the lumen of the stem. Once the retina is reattached, a laser endoprobe is used to apply photocoagulation around the retinal tear.

In another instance, a vitrectomy may be performed to remove a dislocated intraocular lens or an intraocular foreign body. In one embodiment, a device according to the present disclosure is passed through a small gauge trocar or surgical wound. Once inside the eye, the adjuster is used to deploy (e.g., expand) the fiber optic loop. The fiber optic loop is then used to ensnare the intraocular lens or foreign body and remove it from the eye.

In another embodiment, retained lens material following cataract surgery can be chopped using a device according to the present disclosure as a snare. The lens material is first grasped in the fiber optic loop. The adjuster is then used to retract the fiber optic loop back into the stem, causing the lens material to split. The adjuster is then used to re-deploy the fiber optic loop, and the process can be repeated as many times as necessary to reduce the lens material to such a size that it can be removed with a vitreous cutter or simple aspiration.

Figure 4:
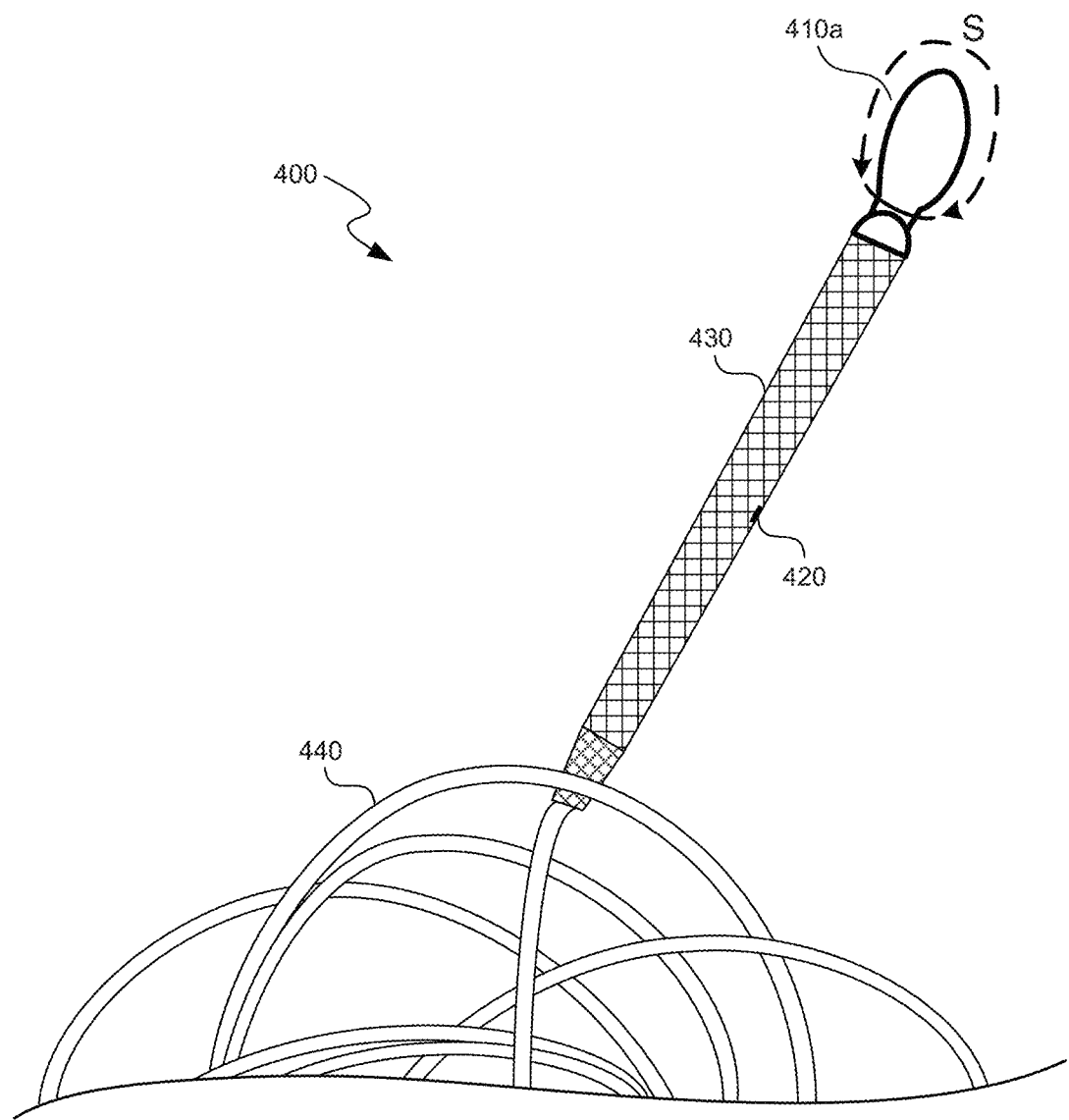
FIG. 4 illustrates another embodiment of a device according to the present disclosure wherein light emanates from the sides of the fiber optic loop.

By adjusting the length or size of the fiber optic loop, a surgeon may change the configuration of the end of the optical fiber itself intraoperatively. In contrast to prior art illumination devices, the device of the present disclosure offers a wider range of illumination options. For example, light emanates from the sides of the devices disclosed herein, rather than from the tip. For example, as shown in FIG. 4, a device 400 consistent with the present disclosure includes an illuminated fiber optic loop portion 410a which extends adjustably from a stem 430. Stem 430 is connected to a fiber optic cable 440 that is in turn operably connected to an adapter (not shown). The adapter is connected to a light source (not shown) which provides light to the optical fiber and the fiber optic loop portion 410a. Movement of adjuster 420 (e.g., a lever) causes size S of the illuminated fiber optic loop portion 410a to expand or shrink. In addition, the fiber optic loop portion of devices of the present disclosure can be used to push or hold tissue during surgery.

With conventional lighting systems, such as a vitrectomy light pipe, the light is directed perpendicular to the surgical field, similar to the way a flashlight is used. This provides bright, focused light for working, but can be too intense when the surgeon needs to hold the light closer to the tissue. Specifically, within the eye, this can lead to too much light, or phototoxicity to retinal photoreceptors and subsequent visual loss. Further, this direct illumination does not highlight the texture of the tissue's surface, which is often desirable during such surgical procedures as epiretinal membrane peeling. To overcome this shortcoming, surgeons may employ the use of vital dyes such as indocyanine green to visualize this tissue better. These dyes can add to the time, cost, and risk of the surgery.

With the present invention, the light supplied during surgery is more diffuse, thus decreasing the risk of phototoxicity to retinal photoreceptors. This is accomplished by using the light that emanates from the sides of the optical fiber, which in an exemplary embodiment may be a loop at the tip of the instrument. This loop can be made larger or smaller during surgery as dictated by the surgeon's needs. Making the loop larger provides more light, and making the loop smaller decreases the light. Further, the loop can be used to light the surface of the retina from an oblique angle, which facilitates visualizing the texture of the retinal surface, thereby decreasing the need for intraoperative vital dyes. Further, the loop of the optical fiber on the device may be used as a second instrument, to hold or push tissue in the eye such as during the repair of a retinal detachment.

Conventional wide-field or chandelier systems provide another illumination option for vitreo-retinal surgeons. Rather than used as an active tool, they are typically placed through the sclera so that the tip penetrates the vitreous cavity. The light delivered by these devices tends to be more diffuse and allows the surgeon to use both hands for holding other instruments. These systems often have a 100 degree field of illumination and are placed at a fixed distance from the retina but cannot provide side illumination to highlight surface texture. Further, chandeliers cast shadows when working instruments are placed in front of them and are also prone to creating glare during air-fluid exchanges such as those required during vitrectomy. Further, chandeliers are often incapable of homogenously illuminating the entire eye, and often need to be repositioned during surgery. Further, the tips of these lights are prone to melting if they come into contact with blood. In addition, the tip of these lights is in a fixed configuration and cannot be adjusted.

In contrast, devices consistent with the present disclosure may have an embodiment whereby it is placed through a fixed point in the sclera similar to a chandelier system. However, the tip of the device which is comprised of a loop of optical fiber connected to an appropriate light source, can be adjusted in size, making the loop larger or smaller to provide more or less light as needed. In one embodiment, the loop could be enlarged to encircle the entire pars plana, providing a diffuse illumination of the surgical field. In another embodiment, trocars could be placed through the pars plana at opposite poles of the eye, and the loop of the optical fiber could be held by these trocars or similar devices, thus allowing a diffuse illumination of the eye's interior. This would eliminate the problems with conventional chandelier systems such as casting shadows or failing to homogenously light the surgical field.

The present device allows surgeons to better visualize tissue, while using lower direct light levels, thereby decreasing the risk of damage to sensitive retinal photoreceptors.

In another embodiment, the device may be used as a stationary, fixed lighting system which is placed through the sclera similar to conventional chandelier lighting systems. For this, the stem is shortened to approximately 2 to 4 mm and connected to a flange which rests outside the eye. The flange prevents the light from migrating during surgery. This can be placed directly through the sclera by the surgeon, or by using conventional trocar placement systems.

During vitrectomy surgery (e.g., to peel membranes from the surface of the retina) the device could be employed to provide a diffuse, oblique illumination of the surface of the tissue. In this way, the presently disclosed device increases the contrast and visibility of the surface compared to conventional direction illumination system, even when directional light sources are used in conjunction with vital dyes.

Further, the diffuse nature of the light delivered by the devices of the present disclosure enables the surgeon to place the light closer to the retina for dynamic visualization without increasing a risk of retinal photoreceptor phototoxicity. In addition, the size of the optical fiber loop can easily be adjusted directly by the surgeon intraoperatively. In addition, the loop at the tip of the device could be used as a second instrument to help stabilize tissue, such as often needed during repair of complex retinal detachments.

Similarly, an alternative embodiment of the current invention in which the device is placed through the sclera at a fixed point in a chandelier-style system can be used during surgery. This allows the surgeon to use both hand for other tools during surgery. The size of the loop at the tip of the chandelier system can similarly be adjusted to allow more or less light as needed. By enlarging the loop so that it circumnavigates the internal diameter of the pars plana, the surgeon can diffusely illuminate the vitreous cavity, thereby avoiding the shadows that typically occur with conventional systems.

Accordingly, in one embodiment the present disclosure provides a method of illuminating ocular tissue, the method comprising providing a device as disclosed herein; optionally increasing the loop length such that the loop portion has a diameter larger than an eye or a portion thereof; placing the loop portion in proximity to the eye; and reducing the loop length such that the loop portion is stationary with respect to the eye. In some embodiments, the loop is placed around at least a portion of the eye, for example the pars plana. Thus, in some embodiments, the loop portion has a diameter larger than a pars plana before placement, and is adjusted (e.g., by movement of an adjuster) to reduce the diameter of the loop portion until it is slightly larger than, about the same size as, or slightly smaller than the pars plana. In some embodiments, the loop portion is placed in proximity to retinal tissue. In some embodiments, the stem comprises a flange portion, and the method further comprising anchoring the device to the eye using the flange. In some embodiments, the method does not include administering a vital dye to the eye.

Figure 5:
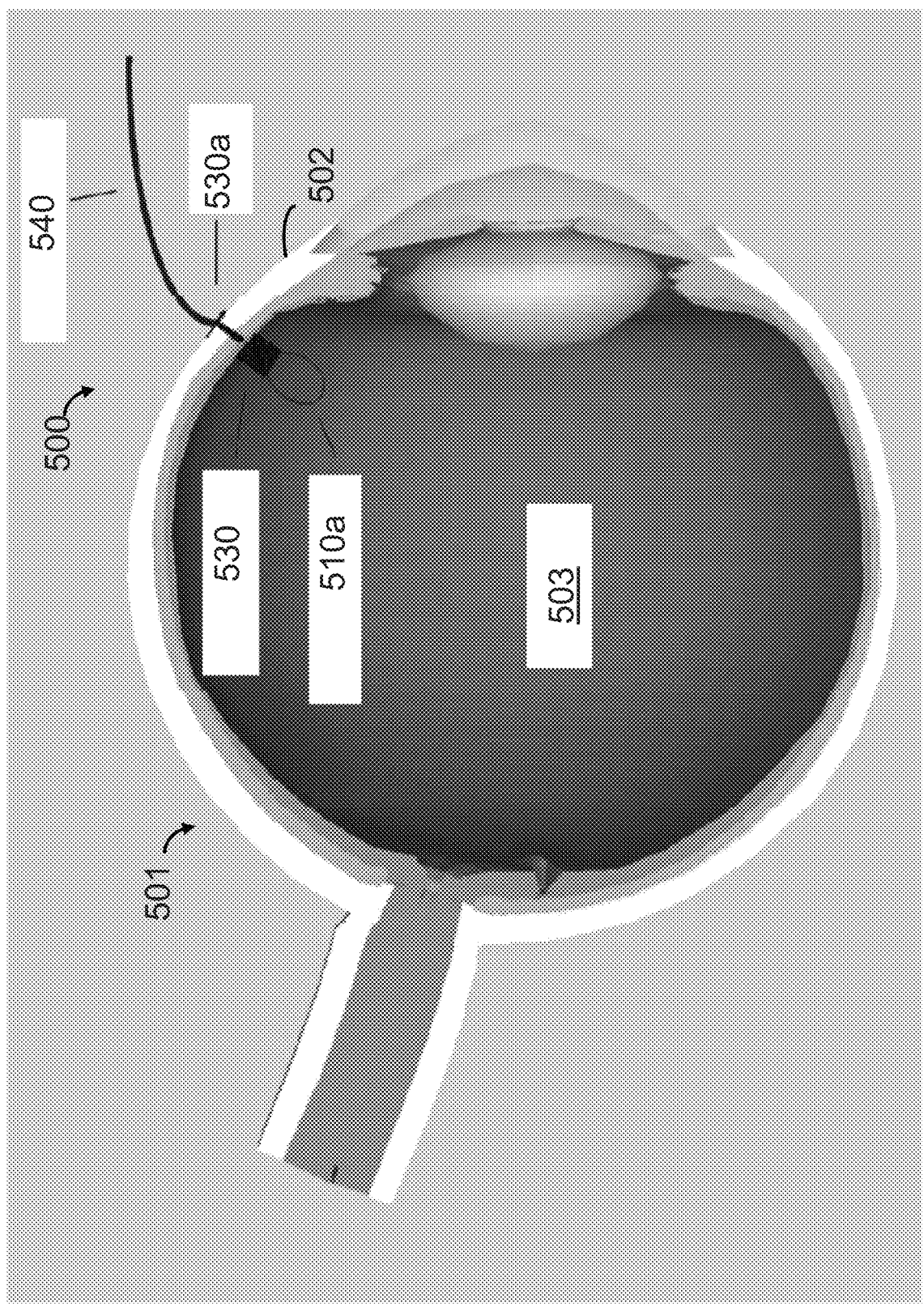
FIG. 5 is a cross sectional view of a device according to the present disclosure during a surgical procedure.

As shown in FIG. 5, a device 500 consistent with the present disclosure includes a stem 530 having a flange 530a. The stem 530 is operably connected to a fiber optic cable 540 housing an optical fiber (not labeled). The optical fiber includes a fiber optic loop portion 510a extending from a proximal end of the stem 530. In the embodiment shown in this figure, device 500 has been placed in an eye 501 such that flange 530a is adjacent to the external surface 502 of the eye 501 (e.g., the sclera), enabling the stem 530 and the fiber optic loop portion 510a to extend through the sclera, choroid and retina and into the vitreous 503.

The invention claimed is:

1. A surgical device comprising an optical fiber forming a loop having at least one side,
   wherein light emanates from the at least one side of the optical fiber loop.

2. The device of claim 1 wherein at least a portion of the optical fiber is housed in a stem.

3. The device of claim 2, wherein a proximal end of the optical fiber is operably coupled to an adjuster.

4. The device of claim 3, wherein the adjuster is configured to adjust a size associated with the loop.

5. The device of claim 1, wherein the adjuster comprises a-lever, a button, a sliding shaft or a sliding cover.

6. The device of claim 1, wherein the device comprises a first configuration wherein light emanates from the loop, and a second configuration wherein light emanates from a tip of the optical fiber.

7. The device of claim 6, wherein the device is configured to convert from the first configuration to the second configuration during surgery.

8. A method of illuminating ocular tissue, the method comprising:
   providing a device according to claim 1;
   increasing loop length such that a loop portion has a diameter larger than an eye or a portion thereof;
   placing the loop portion in proximity to eye or the portion thereof; and
   reducing the loop length such that the loop portion is stationary with respect to the eye.

9. The method of claim 8, wherein the loop portion has a diameter larger than a pars plana.

10. The method of claim 8, wherein the ocular tissue is retinal tissue.

11. The method of claim 8, wherein a stem housing at least a portion of the optical fiber comprises a flange portion configured to anchor the device to the eye using the flange.

12. The method of claim 8, wherein the method does not include administering a vital dye to the eye.

13. A surgical illumination device comprising:
   an optical fiber extending through a lumen and comprising a distal end and a proximal end;
   a stem comprising the lumen, wherein the optical fiber and the proximal end are housed within the lumen to form a loop portion defining a loop length; and
   an adjuster operably coupled to the proximal end, wherein movement of the adjuster causes the loop length to change,
   wherein the distal end of the optical fiber is configured for coupling to a light source such that light emanates from at least one side of the optical fiber of the loop when coupled to the light source.

14. The device of claim 13 further comprising an optical fiber cable surrounding at least a portion of the optical fiber.

15. The device of claim 13, wherein the adjuster is a lever, a button, a sliding shaft or a sliding cover.

16. The device of claim 13, wherein the stem further comprises a flange suitable for anchoring the device in or through ocular tissue.

17. The device of claim 13, wherein the device comprises a first configuration wherein light emanates from a loop, and a second configuration wherein light emanates from a tip of the optical fiber.

* * * * *